United States Patent [19]

Hembersin et al.

[11] 4,362,602

[45] Dec. 7, 1982

[54] PROCESS FOR THE TREATMENT OF HEAVY PRODUCTS RESULTING FROM THE MANUFACTURE OF CHLOROHYDROCARBONS

[75] Inventors: Roland Hembersin, Jemeppe-sur-sambre; Remy Nicaise, Nalinnes, both of Belgium

[73] Assignee: Solvay & Cie., Brussels, Belgium

[21] Appl. No.: 283,188

[22] Filed: Jul. 14, 1981

Related U.S. Application Data

[63] Continuation of Ser. No. 127,260, Mar. 4, 1980, abandoned.

[30] Foreign Application Priority Data

Mar. 12, 1979 [FR] France ................................ 79 06674

[51] Int. Cl.$^3$ ............................................. B01D 3/38

[52] U.S. Cl. ........................................ 203/59; 203/63; 203/95; 570/262

[58] Field of Search ............ 260/652 R, 652 P, 654 S; 203/59, 63, 95–97, 76, 79, 83, 85

[56] References Cited

U.S. PATENT DOCUMENTS 3,803,005  4/1974  Miserlis et al. ...................... 203/97

FOREIGN PATENT DOCUMENTS 418463  8/1974  U.S.S.R. ............................... 203/59

Primary Examiner—Frank Sever
Attorney, Agent, or Firm—Spencer & Kaye

[57] ABSTRACT

A process for the treatment of heavy products resulting from the manufacture of light hydrocarbons. The heavy products are subjected to steam distillation in the presence of a water-soluble surface-active agent.

7 Claims, No Drawings

PROCESS FOR THE TREATMENT OF HEAVY PRODUCTS RESULTING FROM THE MANUFACTURE OF CHLOROHYDROCARBONS

CROSS REFERENCE TO RELATED APPLICATION

This application is a continuation of applicant's copending United States Application Ser. No. 127,260, filed Mar. 4th, 1980, now abandoned.

BACKGROUND OF THE INVENTION

The present invention relates to a process for the treatment of heavy products resulting from the manufacture of chlorohydrocarbons, and more particularly for the treatment of the heavy products resulting from the manufacture of 1,2-dichloroethane, trichloroethylene, perchloroethylene, trichloroethanes or carbon tetrachloride.

In the manufacture of chlorohydrocarbons, heavy products of poorly defined composition are formed which are generally referred to as "tars". These products, which consist mainly of high-boiling chlorohydrocarbons, are found in the stills of the distillation columns used for the separation and purification of the products. In general, they are removed by purging the contents of the stills, but this causes significant losses of utilisable chlorohydrocarbons.

Various techniques have been developed in an attempt to recover the utilisable chlorohydrocarbons present in the purges.

Thus, Belgian Pat. No. 746,200 corresponding to U.S. Pat. No. 3,634,200, filed on 19th proposed that, in the manufacture of 1,2-dichloroethane, the purges be sent from the stills of the 1,2-dichloroethane column into film evaporators in which a mixture of 1,2-dichloroethane and 1,1,2-trichloroethane is recovered as the top fraction and a mixture of heavy chlorinated products is recovered as the bottom fraction; the separation of the latter has no technical or economic advantage and it is burnt. This technique is very difficult to carry out in a continuously operating industrial installation. In fact, the running of a film evaporator is very difficult and the installation must frequently be stopped in order to clean off the deposits and crusts. Moreover, in order to prevent the bottom of the evaporator from becoming fouled too rapidly, it is necessary to restrict the degree of vaporisation to a low percentage, and this does not enable the utilisable products to be recovered in their entirety.

Furthermore, attempts have been made to carry out a steam distillation process. Such a process does indeed enable the recoverable light products to be recovered in the top fraction, but the heavy products remaining in the bottom fraction form an emulsion with the water and this emulsion remains stable even when it is subjected to centrifugation. Since the emulsion obtained, which cannot be burnt because of its high water content and cannot be recycled, cannot be discharged as such into the environment, it has not been possible to use the steam distillation process.

SUMMARY OF THE INVENTION

A process has now been found which does not exhibit the disadvantages of the process using a film evaporator, and which makes it possible to use steam distillation. This process makes it possible to recover, in the top fraction, the desired chlorohydrocarbon and the utilisable chlorination by-products and, as the bottom fraction, an aqueous phase and also an organic phase which contains the non-recoverable heavy products and is perfectly separated from the aqueous phase.

For this purpose, the present invention relates to a process for the treatment of the heavy products resulting from the manufacture of chlorohydrocarbons, in accordance with which process the heavy products are subjected to steam distillation in the presence of a water-insoluble surface-active agent.

The surface-active agent employed according to the invention are water-insoluble products. They are, however, usually soluble in the organic phase containing the heavy products. Preferably, the surface-active agents are chosen from among those which are chemically inert under the acid or alkaline conditions used for carrying out the process. Moreover, they are preferably chosen from among those which do not contain volatile products capable of contaminating the top phase comprising the recoverable organic products. Finally, those surface-active agents having a sufficiently high boiling point to remain in the heavy organic phase recovered in the bottom fraction are preferably chosen.

Water-insoluble surface-active agents are understood as denoting all the surface-active agents which have a solubility in water of less than 1 g/liter when the water is in equilibrium with a solution containing 10 g/liter of surface-active agent in 1,2-dichloroethane at 20° C. The preferred surface-active agents have a solubility of less than 0.8 g/liter under the abovementioned conditions. The best results have been obtained with surface-active agents which have a solubility, as defined above, of less than 0.5 g/liter.

The choice of water-insoluble surface-active agents is an essential characteristic of the invention. In fact, it has been found that other surface-active agents cause the formation of emulsions of water with heavy chlorinated products, which emulsions are stable or even more stable than the emulsions in which no surface-active agents are present.

The surface-active agents used according to the invention are normally chosen from amongst those of which the hydrophilic/lipophilic balance (HLB), as defined by P. Blonchard in PARF. COSM. SAV., Volume 12, No. 2, of February 1969, pages 82–91, and expressed by the equation $$HLB = \frac{1 \times \text{molecular weight of the hydrophilic part} \times 100}{5 \times \text{total molecular weight}}$$

is equal to at most 9. Preferably, the surface-active agents used according to the invention have a HLB of between 4 and 7. The best results have been obtained with surface-active agents having a HLB of between 5 and 6.

The surface-active agents used are most frequently chosen from among mono- or poly-oxyethyleneated fatty amines, fatty alcohols, alkylphenols, fatty acids and fatty acid amides, fatty acid esters, condensates of ethylene oxide and of propylene oxide, and ethanolamides.

Among the surface-active agents listed above, the ethoxylated fatty amines are particularly suitable, and the best results have been obtained with mono-, di- and tri-oxyethyleneated fatty amines. More particularly, the process is preferably carried out with amines having the general formula

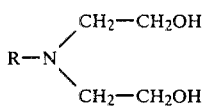

in which R represents saturated or unsaturated alkyl radicals having from 12 to 24 carbon atoms. The most suitable compounds are those in which R possesses from 16 to 20 carbon atoms. The best results have been obtained with amines in which R possesses 18 carbon atoms.

The amount of surface-active agent to be employed according to the invention is chosen with regard to the origin and the nature of the heavy chlorinated products to be treated. In general, the surface-active agent is employed at a rate of 0.001 to 20 grams per kilogram of heavy products to be treated, and preferably at a rate of 0.005 to 10 grams per kilogram. Particularly advantageous results have been obtained with amounts ranging from 0.01 to 5 g of surface-active agent per kg of heavy chlorinated product to be treated. The use of excessively large amounts of surface-active agent can, under certain circumstances, generate stable emulsions of water with heavy chlorinated products. In such cases, the amount of surface-active agent should be reduced.

Several different surface-active agents can be employed simultaneously according to the invention. In this case, however, the HLB index of the mixture preferably satisfies the conditions defined above, and each of the compounds constituting the mixture should have a solubility in water which satisfies the solubility conditions defined above.

The surface-active agent can be introduced into the heavy products before or after they have been subjected to steam distillation. A particularly advantageous procedure consists in introducing the surface-active agent directly into the heavy products to be treated, before or during the steam distillation. This latter embodiment makes it possible to carry out the process according to the invention with the minimum number of manipulations and minimum energy losses.

The surface-active agent can be introduced continuously or discontinuously into the heavy products to be treated.

The heavy chlorinated products treated according to the invention are products of poorly defined composition which are also referred to as "tars". These products generally consist of a group of high-boiling polychlorinated by-products; all these by-products are generally present in small concentrations and this renders their recovery and separation difficult and generally non-viable from an industrial point of view.

The heavy chlorinated products which can be treated according to the invention can have diverse origins. In general, they result from the manufacture or purification of light chlorinated products of one and the same origin or of different origins. Light chlorinated products are understood as meaning aromatic chlorinated compounds containing fewer than 10, and preferably from 6 to 8, carbon atoms, and saturated or unsaturated, straight-chain or branched-chain, cyclic or non-cyclic, chlorinated aliphatic compounds containing fewer than 8, and preferably fewer than six, carbon atoms.

The process according to the invention is advantageously applied to the heavy chlorinated products resulting from the manufacture of aliphatic compounds having fewer than 4 carbon atoms, and more particularly from the manufacture of vinyl chloride, 1,2-dichloroethane, trichloroethylene, perchloroethylene, trichloroethanes and chloromethanes. Very good results have been obtained when the process is applied to the heavy chlorinated products resulting from the manufacture of 1,2-dichloroethane.

The heavy chlorinated products can be subjected to various chemical or physical treatments before, during or after the steam distillation. Thus, for example, it is possible to introduce a basic compound into the heavy products to be subjected to steam distillation, in order to avoid excessive acidification of the medium due to the formation of hydrochloric acid generated by the decomposition of certain unstable chlorinated organic compounds under the operating conditions.

The steam distillation can be carried out by any technique known for this purpose. The steam distillation operation is not in itself critical for the present invention. The temperature and the pressure of the steam introduced into the heavy chlorinated products are generally chosen in accordance with the nature of the latter. These parameters are not in themselves critical and are those which are normally used in steam distillation techniques.

The steam distillation is generally carried out for a duration which is such that at least 20% by volume of the light starting products are distilled and recovered in the form of a top distillation product. This degree of distillation is not in itself critical and can vary in accordance with the composition of the heavy chlorinated products treated. Thus, if the heavy chlorinated products contain a large amount of recoverable and utilisable light products, a higher degree of distillation is chosen. In the recovery of the by-products from the manufacture of 1,2-dichloroethane, the process is generally carried out with a degree of distillation of between 25% and 85%; the degree of distillation advantageously varies between 35% and 80%.

The top fraction collected in the process according to the invention consists of an organic fraction and a separate aqueous phase. The organic fraction generally comprises the main product of the initial manufacturing process and the main light by-products of this manufacturing process. These organic products are finally separated in the distillation columns of the initial cycle for manufacturing the light chlorinated products, to which distillation columns the top fraction is recycled. The aqueous phase collected in the top fraction is more than 99% pure.

By virtue of the addition of the surface-active agent, the bottom fraction remaining after the steam distillation operation also consists of two well-separated phases. The organic phase consists of heavy chlorinated residues which are currently non-recoverable and which can be stored for possible subsequent use or can be destroyed by means normally used for this purpose, such as burning at sea. The separate aqueous fraction recovered in the bottom fraction is more than 99% pure, just as is the aqueous phase collected in the top fraction. Consequently, the aqueous phases collected in the top and bottom fractions can advantageously be re-used in a further steam distillation cycle.

The following examples are given by way of illustration, and are not to be understood as limiting the scope and underlying principles of the invention in any way.

EXAMPLE 1

100 cm³ (125 g) of heavy chlorinated products resulting from the manufacture of 1,2-dichloroethane, the composition of which, as determined by vapour phase chromatography, is given in Table 1, and 0.5 g, per liter of heavy chlorinated products employed, of the surface-active agent TENSOXID S20, which is sold by the Company TENSIA and which is a product resulting from the condensation of ethylene oxide with tallow amine, are introduced into a 1 liter Wülff flask.

The flask is then heated to 90° C. and steam under atmospheric pressure is passed continuously through the mixture of heavy chlorinated products in accordance with the well-known steam distillation technique. The organic product distilled by the steam is condensed and recovered in a 200 cm³ graduated cylinder. The distillation is stopped when the cylinder contains 75 cm³ of distilled chlorinated products (degree of distillation: 75%). The separate organic and aqueous fractions collected at the top and the separate organic and aqueous fractions collected at the bottom of the 1 liter flask are then analysed by vapour phase chromatography and the results are summarised in Table 1.

TABLE 1

| Compounds | Composition of heavy product amount g | Composition of heavy product content g/kg | TOP FRACTION Organic phase amount g | TOP FRACTION Organic phase content g/kg | TOP FRACTION Aqueous phase amount g | TOP FRACTION Aqueous phase content g/kg | BOTTOM FRACTION Organic phase amount g | BOTTOM FRACTION Organic phase content g/kg | BOTTOM FRACTION Aqueous phase amount g | BOTTOM FRACTION Aqueous phase content g/kg |
|---|---|---|---|---|---|---|---|---|---|---|
| 1,2-dichloroethane | 25.0 | 200 | 24.38 | 260 | 0.06 | 2.1 | 0.34 | 11.0 | 0.03 | 0.45 |
| 1,1,2-trichloroethane | 55.38 | 443 | 44.91 | 479 | 0.05 | 1.8 | 9.22 | 295 | 0.14 | 2.0 |
| 1,3-dichloropropane | 1.23 | 9.8 | 0.76 | 8.1 | <0.01 | 0.02 | 0.12 | 3.7 | — | — |
| 3,4-dichlorobut-1-ene | 0.48 | 3.8 | 0.34 | 3.6 | — | — | — | — | — | — |
| 1,2-dichlorobutane | 2.63 | 21 | 1.50 | 16.0 | <0.01 | 0.01 | 0.47 | 15.0 | <0.01 | 0.03 |
| various unidentified and identified | 24.28 | 194.4 | 16.69 | 178.0 | <0.01 | 0.02 | 4.09 | 131 | 0.06 | 0.89 |
| heavy compounds | 16 | 128 | 5.18 | 55.2 | <0.01 | 0.15 | 17.0 | 544 | 0.02 | 5.4 |
| TOTAL | 125.0 | | 93.76 | | 0.12 | | 31.24 | | 0.43 | |

The conversions from g/kg to g were carried out by comparing the specific weight of the heavy compounds with that of 1,2-dichloroethane (1.25). The various compounds consist, in particular, of perchloroethylene, cis-1,3-dichlorobutene, trans-1,3-dichlorobutene, 1,1,1,2-tetrachloroethane and 1,1,2-trichloropropane. The aqueous phase recovered in the top fraction also contains 0.03 g of products which are lighter than 1,2-dichloroethane (methylene chloride, 1,1-dichloroethane, chloroform and cis- and trans-1,2-dichloroethylene).

EXAMPLE 2

Example 1 was repeated but heavy chlorinated products of a different origin, obtained from a process for the manufacture of 1,2-dichloroethane, were used as the starting materials and the content of surface-active agent TENSOXID S20 was 1 g/liter of heavy chlorinated products employed.

The operating conditions are the same as those of Example 1, except for the degree of distillation, which was restricted to 50%.

The results obtained are summarised in Table 2 below.

TABLE 2

| Compounds | Composition of heavy product amount g | Composition of heavy product content g/kg | TOP FRACTION Organic phase amount g | TOP FRACTION Organic phase content g/kg | TOP FRACTION Aqueous phase amount g | TOP FRACTION Aqueous phase content g/kg | BOTTOM FRACTION Organic phase amount g | BOTTOM FRACTION Organic phase content g/kg | BOTTOM FRACTION Aqueous phase amount g | BOTTOM FRACTION Aqueous phase content g/kg |
|---|---|---|---|---|---|---|---|---|---|---|
| light | 1.58 | 12.6 | 1.16 | 18.6 | — | — | 1.49 | 23.8 | 0.12 | 2.3 |
| 1,2-dichloroethane | 19.5 | 156 | 17.37 | 278 | 0.03 | 2.46 | 2.94 | 47 | 0.01 | 0.53 |
| intermediate | 0.25 | 2.0 | 0.15 | 2.5 | — | — | 0.11 | 1.7 | — | — |
| trichloroethylene | 0.11 | 0.9 | 0.04 | 0.7 | — | — | 0.06 | 1.0 | — | — |
| 1,1,2-trichloroethane | 65.6 | 525 | 33.1 | 530 | 0.04 | 2.74 | 31.9 | 511 | — | — |
| perchloroethylene | 8.75 | 70 | 4.81 | 77 | <0.01 | 0.02 | 3.69 | 59 | — | — |
| 1,1,1,2-tetrachloroethane | 6.75 | 54 | 2.19 | 35 | — | — | 4.06 | 65 | — | — |
| 1,1,2,2-tetrachloroethane | 5.5 | 44 | 1.38 | 22 | — | — | 3.75 | 60 | — | — |
| 1,4-dichlorobutane | 6.63 | 53 | 1.19 | 19 | — | — | 5.72 | 90 | — | — |
| heavy | 10.15 | 81 | 1.19 | 19 | — | — | 8.81 | 141 | — | — |
| TOTAL | 125.0 | | 62.58 | | 0.07 | | 62.43 | | 0.13 | |

The conversions from g/kg to g were carried out by comparing the specific weight of the heavy compounds with that of 1,2-dichloroethane (1.25). The light compounds are products of the chloroform and 1,1- dichloroethane type. The intermediate and heavy compounds are products which have not been identified.

It can be deduced from the results observed that the separation into different separable phases is virtually perfect and that the recovery of recoverable light products (1,2-dichloroethane and 1,1,2-trichloroethane) is respectively 99% and 80% for a degree of distillation of 75% (Example 1); these values still reach 90% and 55% for a degree of distillation of not more than 50% (Example 2). Moreover, the aqueous phases obtained are virtually pure.

What is claimed is:

1. In a process for the treatment of the heavy products resulting from the manufacture of chlorohydrocarbons, which products consist essentially of high-boiling chlorohydrocarbons found in the stills of distillation columns used for the separation and purification of chlorohydrocarbons, in which the heavy products are subjected to steam distillation to form a top fraction comprising light chlorinated products and a bottom fraction comprising high boiling chlorohydrocarbons, the improvement comprising carrying out the distillation in the presence of a water-insoluble surface-active agent having a solubility in water of less than 1 gram per liter when the water is in equilibrium with a solution containing 10 grams per liter of surface-active agent in 1,2-dichloroethane at 20° C.; said solubility being sufficiently low to substantially preclude formation of an emulsion between said high boiling chloroydrocarbons and water.

2. Process according to claim 1, wherein said heavy products result from the manufacture of 1,2-dichloroethane.

3. Process according to claim 1 or 2, wherein the surface-active agent possesses a HLB index between 4 and 7.

4. Process according to claim 1 or 2, wherein a mono-, di- or tri-oxyethyleneated fatty amine is used as said surface-active agent in a quantity of 0.005 to 10 grams per kilogram of heavy product treated.

5. Process according to claim 4 wherein said oxyethyleneated fatty amine is of the general formula

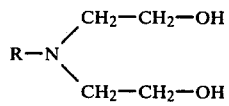

in which R represents an alkyl radical having from 16 to 20 carbon atoms.

6. Process according to claim 5, wherein R is an alkyl radical having 18 carbon atoms.

7. Process according to claim 1 or 2, wherein the surface-active agent is employed at a rate of 0.005 to 10 grams per kilogram of heavy product treated.

* * * * *